United States Patent [19]

Neale

[11] 4,079,071

[45] Mar. 14, 1978

[54] SYNTHESIS OF HYDROSILANES FROM METHYLCHLOROPOLYSILANES

[75] Inventor: Robert Schwenn Neale, Ossining, N.Y.

[73] Assignee: Union Carbide Corporation, New York, N.Y.

[21] Appl. No.: 781,993

[22] Filed: Mar. 28, 1977

[51] Int. Cl.$^2$ .......................... C07F 7/08; C07F 7/12; C01B 33/08; C01B 33/04
[52] U.S. Cl. .............................. 260/448.2 E; 423/324; 423/342; 423/347
[58] Field of Search ................. 260/448.2 E; 423/342, 423/347, 324

[56] References Cited

U.S. PATENT DOCUMENTS

| | | | |
|---|---|---|---|
| 2,787,627 | 4/1957 | Kuriyagawa et al. | 260/448.2 E |
| 3,432,537 | 3/1969 | Guinet et al. | 260/448.2 E |
| 3,639,105 | 2/1972 | Atwell et al. | 260/448.2 E X |
| 3,878,234 | 4/1975 | Atwell et al. | 260/448.2 E |

*Primary Examiner*—Paul F. Shaver
*Attorney, Agent, or Firm*—Reynold J. Finnegan

[57] ABSTRACT

The present invention relates to a process for preparing high yields of hydrosilanes by reacting methylchloropolysilanes with hydrogen gas under pressure at a temperature of from about 25° C to about 350° C in the presence of a copper catalyst. Useful copper catalysts include copper metal, copper salts, and complexes of copper salts with organic ligands.

8 Claims, No Drawings

SYNTHESIS OF HYDROSILANES FROM METHYLCHLOROPOLYSILANES

BACKGROUND AND DESCRIPTION OF THE PRIOR ART

Hydrogenation catalysts for polysilanes are well known in the art. These include both metals and metal salts, which are insoluble in the polysilane reactants, and metal complexes containing organic ligands, which are soluble in the polysilane reactants. However, hydrogenation catalysts disclosed in the prior art generally contain palladium, ruthenium, rhodium, platinum or nickel. Although copper metal, copper salts and copper complexes are well known as catalysts for a wide variety of reactions, most of which are oxidative in nature (see L. F. Fieser and M. Fieser, *Reagents For Organic Synthesis*, pp. 155–170 (1967)) they have not been considered to be useful as hydrogenation catalysts unless combined with chromium.

For example, U.S. Pat. No. 3,639,105 discloses the preparation of hydrosilanes from alkyl-substituted disilanes and halogen-substituted disilanes by hydrogenation of the disilane at a temperature of from 25° C to 250° C in the presence of a catalyst. The catalysts useful in the process of that patent are Group VIII transition metal catalysts, including organophosphine complexes of those transition metals.

Another publication (see H. Gilman and G. L. Schwebke, "Advances in Organometallic Chemistry", 1, 89 (1964)) discloses the hydrogenation of an unusual cyclic tetraphenyltetrasilane using an initial hydrogen pressure of 800 psi and a reaction temperature of 150° C using a copper chromite catalyst. At the same reaction conditions, hexaethyldisilane failed to cleave. No disclosure was made of the use of a copper catalyst without chromium. The reactivity of halogen-containing polysilanes was not investigated.

Another publication (*Chemical Abstracts*, 53, 17888 (1959)) discloses the cleavage of the Si-Si bond in methylchlorodisilanes using disilanes in the vapor phase over 5% KOH/Al$_2$O$_3$ at 500° C to give monosilanes.

SUMMARY OF THE INVENTION

The present invention relates in part to a process for preparing high yields of hydrosilanes by reacting methylchloropolysilanes with hydrogen gas under pressure at a temperature of from about 25° C to about 350° C.

The process for production of the hydrosilanes that is disclosed in this invention is characterized by a copper catalyst. Useful copper catalysts include copper metal, copper salts, and complexes of copper salts with organic ligands.

DESCRIPTION OF THE PREFERRED EMBODIMENTS

This invention relates to a process for preparing silanes of the formula H$_a$Me$_x$SiCl$_{4-(a+x)}$, comprising A. contacting
  (1) a polysilane consisting of units of the formula:

Me$_x$Cl$_y$Si  (I), with
  (2) hydrogen gas under pressure, and

B. heating the above admixture to a temperature of from about 25° C to about 350° C, in the presence of a catalytic amount of a copper catalyst, wherein $a$ is 1 to 2, $x$ is 0 to 3, and $y$ is 0 to 3, the sum of $a$ and $x$ being from 1 to 4, the sum of $x$ and $y$ being from 1 to 3; all the silicon atoms in (I) being bonded to at least one other silicon atom and all the valences of the silicon atoms in (I) being satisfied by other silicon atoms, Cl or Me radicals, with the proviso that the polysilane contain at least one Cl group.

The process of this invention is carried out by reacting (1) and (2) in the presence of the copper catalyst at a temperature of from about 25° C to about 350° C. However, to effect the reaction within a reasonable time period of, for example, less than 10 hours, the preferred temperature range is about 100° C to about 350° C. Above 350° C, copper catalyst and/or polysilane decomposition may occur, adversely affecting the reaction. Although initial hydrogen pressures of 100 psig or lower may be employed according to the process of the invention, a preferred range of initial hydrogen pressures is from about 500 psig to about 1000 psig. Reaction time is generally less than 10 hours, but it may be longer if desired for some purpose. The preferred reaction time is about 1 hour to about 6 hours.

The process of the invention can be carried out in the presence or absence of a solvent. The amount of solvent employed, if used, is not critical and the primary purpose of the solvent is to facilitate handling of the reaction mixture. If employed, the solvents are those which do not react with chlorosilanes or hydrogen (i.e., inert to the reactants employed in the invention) and can be any such solvent such as linear, cyclic or branched-chain hydrocarbons such as pentane, 2-methylpentane, hexane, cyclohexane, octane and isoctane.

The term "copper catalyst" is intended to include materials wherein the only metal is copper, such as copper metal (e.g., copper powder), copper salts such as copper chlorides (e.g., cuprous and cupric chloride), and copper salts containing organic ligands such as tetramethylethylenediamine copper chloride. Useful cations in the copper salt catalysts of the invention include both Cu(I) and Cu(II), and useful counterions include halide, oxide, sulfide, sulfate, nitrate, hexafluorophosphate, and carbonate. The preferred anion is chloride.

The term "copper catalyst" is also intended to encompass complexes of copper salts with organic ligands such as the product of the reaction of two moles of tributylphosphine with one mole of cupric chloride. Such complexes are prepared by adding the organic compound (e.g., tributylphosphine) to an alcoholic or aqueous/alcoholic solution of copper metal salt and isolating the product.

The amount of copper catalyst employed in the process of this invention is not narrowly critical as long as a catalytically effective amount is present. For purposes of the invention, the amount of copper catalyst present must be at least about 0.2 wt. percent based upon the weight of the polysilane reactant.

The hydrogen gas under pressure useful in the process of the present invention may be fed into the reactor in a single charge. Alternatively, a continuous feed of hydrogen under relatively low pressure (e.g., > 1 atmosphere) into the reactor during the course of the reaction may be made.

The polysilanes which are useful in the process of the present invention are well known in the art. For example, polysilane by-products of the reaction of methyl chloride with silicon metal include $Cl_2CH_3SiSiCH_3Cl_2$, $Cl_2CH_3SiSi(CH_3)_2Cl$, and $Cl(CH_3)_2SiSi(CH_3)_2Cl$. Also, hexachlorodisilane and octachlorotrisilane are by-products in the commercial preparation of trichlorosilane from silicon metal and hydrogen chloride. Thus, specific examples of useful polysilanes include: hexachlorodisilane, 1,1-dimethyltetrachlorodisilane, 1,2-dimethyltetrachlorodisilane, 1,1,2-trimethyltrichlorodisilane and 1,1,2,2-tetramethyldichlorodisilane. Also useful are polymeric silanes having more than two silicon atoms such as, 1,1,2,3-tetramethyltetrachlorotrisilane, octachlorotrisilane and dodecylchloropentasilane.

The process of the present invention involves a reaction in which cleavage of the silicon-silicon bond in the above-mentioned polysilanes takes place to form two silicon-hydrogen bonds to produce $H_aMe_xSiCl_{4-(a+x)}$ wherein $a$ and $x$ are defined above.

The following examples are given by way of illustration only in order to describe the invention in greater detail, and are not intended to limit the scope thereof.

As used herein, "Me" denotes the methyl group, "%" denotes weight percent, and "psig" denotes pounds per square inch gauge.

EXPERIMENTAL

Preparation of Soluble Copper Catalysts

Certain of the copper catalysts useful in the process of the present invention, namely, those catalysts containing an organic ligand, are soluble in the polysilane reactant mixture. These catalysts are prepared by adding the organic ligand dissolved in methanol to a methanolic solution of a metal chloride at room temperature. Solid catalyst products were collected by filtration. Liquid catalyst products, such as the tributylphosphine complex of copper chloride, were obtained by removing the solvent under vacuum.

EXAMPLE 1

Except as otherwise noted in Table I below, the following polysilane reactant charge was used in Runs 1 to 47:

| Charge Component | Weight Percent Of Total Charge |
|---|---|
| $Cl_2MeSiSiMeCl_2$ | 56.7 |
| $Cl_2MeSiSiMe_2Cl$ | 29.7 |
| $ClMe_2SiSiMe_2Cl$ | 5.2 |
| $Me_2SiSiMeCl_2$ | 3.5 |
| $Me_3SiSiMe_2Cl$ | 5.4 |
| Others | 3.5 |

A charge of polysilanes equal to about 43 – 45 grams was introduced into a 300 milliliter stainless steel rocking autoclave which had first been cleaned with an abrasive cleanser and wire brush and then dried and purged with nitrogen. Next, solid or liquid catalyst was added to the polysilane mixture, the autoclave was pressurized with hydrogen, rocking of the autoclave was begun, and heat was applied to the mixture through an external jacket. The temperature was raised to the desired point and maintained for the period of time shown in Table I. The autoclave was allowed to cool sufficiently to prevent loss of volatile products, vented, and opened in order to recover the product mixture.

Using an alternative procedure when there was a ten-fold scale-up of reactants and a 3-liter autoclave was used (see Run 17, Table I below), the product mixture was obtained from the autoclave by displacement through a dip tube utilizing residual internal gas pressure in the autoclave.

The product yields, expressed as weight percents based on the total amounts of polysilane reactant charge, were determined by gas chromatography. Although not shown in the results presented in Table I, trace amounts of $H_3MeSi$ were observed in most of the reactions. The results are presented in Table I which follows.

TABLE I

THE CATALYTIC SYNTHESIS OF HYDROSILANES FROM POLYMETHYLCHLOROSILANES

| No. | Catalyst Compound | wt-% Catalyst | Psig H$_2$ | °C | Hr | % Convers. | Me$_2$SiCl$_2$ | MeSiCl$_3$ | Me$_3$SiCl | HMeSiCl$_2$ | HMe$_2$SiCl | H$_2$MeSiCl | Total | Hydro silanes | Wt-%$^d$ residues | Additive Compound | Wt-% |
|---|---|---|---|---|---|---|---|---|---|---|---|---|---|---|---|---|---|
| 1 | None | — | 1000$^b$ | 350 | 5.5 | 60 | 6 | 6 | NA$^c$ | 0 | 0 | NA | 12 | 0 | 48 | | |
| 2 | None | — | 1000 | 350 | 1. | 50 | 8 | 8 | NA | 4 | tr$^e$ | NA | 20 | 4 | 30 | | |
| 3 | None | — | 1000 | 275 | 5. | 5 | NA | NA | NA | NA | NA | NA | NA | NA | NA | | |
| 4 | (φ$_3$P)$_2$PdCl$_2$ | 0.3 | 1000 | 275 | 5. | 30 | 1 | 5 | NA | 4 | tr$^e$ | NA | 10 | 4 | 20 | | |
| 5 | (φ$_3$P)$_2$PtCl$_2$ | 0.35 | 1000 | 275 | 5. | 10 | 1 | 2 | NA | 4 | 1 | NA | 8 | 5 | 2 | | |
| 6 | (φ$_3$P)$_3$PtCl$_2$ | 0.35 | 1000 | 350 | 1. | 45 | 3 | 2 | NA | 3 | tr$^e$ | NA | 10 | 3 | 35 | | |
| 7 | (φ$_3$P)$_3$RuCl$_2$ | 0.4 | 1000 | 275 | 2.5 | 25 | 1 | 4 | NA | 1 | tr | NA | 5 | 1 | 20 | | |
| 8 | (φ$_3$P)$_3$Rh(CO)Cl | 0.4 | 1000 | 275 | 5. | 10 | 2 | 4 | NA | 3 | 1 | NA | 10 | 4 | 0 | | |
| 9 | Co$_2$(CO)$_8$ | 0.8 | 1000 | 350 | 1. | 25 | 5 | 4 | NA | 2 | 0 | NA | 12 | 2 | 13 | | |
| 10 | CoS$_x$ | 1.2 | 1000 | 350 | 1. | 59 | 10 | 5 | 4 | 14 | 3 | 4 | 46 | 21 | 13 | | |
| 11 | Copper chromite | 0.5 | 1000 | 275 | 17.5 | 40 | 3 | 11 | NA | 15 | 3 | NA | 23 | 18 | 17 | | |
| 12 | Copper chromite | 0.2 | 1000 | 350 | 1. | 70 | 11 | 2 | NA | 18 | 2 | NA | 37 | 20 | 33 | | |
| 13 | Copper chromite | 0.2 | 1000 | 350 | 16. | 100 | 18 | 6 | NA | 32 | 6 | NA | 67 | 38 | 33 | | |
| 14 | CuCl | 1. | 1000 | 350 | 1. | 96 | 22 | 11 | 4 | 39 | 7 | 14 | 95 | 60 | 0 | | |
| 15$^b$ | CuCl | 1. | 1000 | 355 | 1. | 96 | 20 | 11 | 4 | 34 | 8 | 13 | 90 | 55 | 6 | | |
| 16$^g$ | CuCl | 1. | 1000 | 340–60 | 1. | 91 | 23 | 12 | 3 | 32 | 7 | 12 | 89 | 51 | 2 | | |
| 17$^h$ | CuCl | 1. | 1000 | 325 | 2. | 82 | 14 | 6 | 3 | 34 | 8 | 11 | 76 | 53 | 6 | | |
| 18 | CuCl | 1. | 1000 | 350 | 3. | 98 | 26 | 16 | 2 | 27 | 6 | 7 | 85 | 40 | 13 | | |
| 19 | CuCl | 1. | 1000 | 350–75 | 1. | 96 | 14 | 8 | 3 | 22 | 4 | 9. | 59 | 35 | 37 | | |
| 20 | Cu powder | 0.44 | 1000 | 350 | 1. | 96 | 15 | 6 | 1 | 37 | 8 | 10 | 79 | 55 | 17 | | |
| 21 | Cu powder | 0.11 | 1000 | 350 | 1. | 28 | 6 | 3 | 1 | 7 | 1 | 1 | 19 | 9 | 9 | | |
| 22 | CuCl | 1. | 1000 | 350 | 1. | 88 | 17 | 9 | 3 | 34 | 8 | 11 | 82 | 53 | 6 | AlCl$_3$ | 0.33 |
| 23 | CuCl | 1. | 1000 | 280 | 5. | 24 | 7 | 1 | 2 | 12 | 1 | 2 | 24 | 15 | 0 | AlCl$_3$ | 0.33 |
| 24 | CuCl | 1. | 1000 | 325 | 2. | 98 | 33 | 9 | 2 | 27 | 7 | 11 | 89 | 45 | 9 | AlCl$_3$ | 1.3 |
| 25 | CuCl | 1. | 1000 | 360 | 1.3 | 66 | 5 | 7 | 2 | 22 | 5 | 7 | 46 | 34 | 20 | ZnCO$_3$ | 0.32 |
| 26 | CuCl | 1. | 1000 | 350 | 1.8 | 54 | 11 | 8 | tr | 6 | 2 | 1 | 29 | 8 | 25 | ZnCO$_3$ | 1.3 |
| 27 | 30/70 Cu/Si alloy | 2.2 | 1000 | 340–60 | 4. | 99 | 20 | 11 | 4 | 36 | 7 | 15 | 93 | 58 | 6 | — | |
| 28 | NP Raney Ni$^i$ | 0.4 | 1000 | 350 | 6. | 95 | 18 | 8 | 3 | 37 | 8 | 13 | 87 | 58 | 8 | Me$_4$Si | 13. |
| 29 | NP Raney Ni | 0.4 | 1000 | 350 | 4. | 97 | 20 | 9 | 7 | 33 | 7 | 15 | 91 | 55 | 6 | — | |
| 30 | Ni,Zr on kieselguhr$^j$ | 1.1 | 1000 | 350 | 6. | 95 | 15 | 16 | 3 | 29 | 8 | 14 | 85 | 51 | 10 | — | |
| 31 | Ni on kieselguhr$^k$ | 1.1 | 1000 | 350 | 6. | 80 | 14 | 15 | 2 | 24 | 7 | 13 | 75 | 44 | 5 | — | |
| 32 | (MeOCH$_2$CH$_2$OMe)NiCl$_2$ | 0.7 | 1000 | 350 | 1.3 | 66 | 12 | 7 | 2 | 25 | 5 | 7 | 58 | 37 | 8 | — | |
| 33 | (Bu$_3$P)$_2$PdCl$_2$ | 1. | 500 | 120 | 4. | 49 | tr | 8 | tr | 20 | tr | tr$^e$ | 28 | 20 | 21 | — | |
| 34 | (Bu$_3$P)$_2$PdCl$_2$ | 1. | 600 | 150 | 6. | 72 | 5 | 23 | tr | 17 | 1 | tr$^e$ | 46 | 18 | 26 | — | |
| 35 | 2Bu$_3$P.CuCl$_3$ | 2. | 500 | 200 | 4. | 84 | 15 | 13 | 2 | 36 | 1 | 10 | 77 | 47 | 7 | — | |
| 36 | 2Bu$_3$P.CuCl$_2$ | 1. | 600 | 150 | 6. | 84 | 16 | 12 | 2 | 43 | 1 | 12 | 86 | 56 | 0 | — | |
| 37 | CuCl$_2$ | 0.26 | 750 | 150 | 6. | 78 | 16 | 29 | 1 | 1 | 0 | 0 | 47 | 1 | 31 | Bu$_2$P | 1.5 |
| 38 | 2φBu$_2$P.CuCl$_2$ | 1. | 750 | 150 | 6. | 67 | 11 | 18 | 2 | 5 | 0 | tr$^e$ | 36 | 5 | 31 | — | |
| 39 | 2φ$_2$P.CuCl$_2$ | 1. | 600 | 150 | 6. | 28 | 1 | 1 | tr | tr | 0 | 0 | 2 | 0 | 26 | — | |
| 40 | (Me$_2$NCH$_2$CH$_2$NMe$_2$)CuCl$_2$ | 1. | 600 | 150 | 22. | 75 | 10 | 22 | 1 | 15 | tr | 1 | 48 | 16 | 27 | — | |
| 41 | (C$_{16}$H$_{33}$NMe$_2$)CuCl$_3$ | 1. | 600 | 150 | 6 | 45 | 1 | 8 | tr | 4 | 0 | tr | 13 | 4 | 32 | — | |
| 42 | (acac)$_2$Cu | 1. | 600 | 150 | 6. | 4 | 1 | 1 | tr | 1 | 0 | 0 | 3 | 1 | 1 | — | |
| 43 | (Bu$_3$P)$_2$NiCl$_2$ | 2. | 1000 | 200 | 4. | 84 | 7 | 14 | 1 | 30 | 4 | 8 | 64 | 42 | 20 | — | |
| 44 | (Bu$_3$P)$_2$PdCl$_2$ | 1. | 600 | 150 | 6.5 | 86 | 17 | 15 | 2 | 37 | tr$^e$ | 13 | 84 | 50 | 2 | — | |
| 45 | (Bu$_3$P)$_2$NiCl$_2$ | 1. | 600 | 100 | 6.5 | 86 | 16 | 11 | 2 | 43 | tr$^e$ | 11 | 84 | 54 | 2 | — | |
| 46 | (Bu$_3$P)$_2$NiCl$_2$ | 0.5 | 750 | 100 | 3.0 | 84 | 16 | 10 | 2 | 43 | 2 | 11 | 84 | 54 | 0 | — | |

TABLE I-continued
THE CATALYTIC SYNTHESIS OF HYDROSILANES FROM POLYMETHYLCHLOROSILANES

| No. | Catalyst Compound | wt-% Catalyst | Psig $H_2$[b] | °C | Hr | % Convers. | Wt-% yield monomers[a] | | | | | | Total | Hydro silanes | Wt-%[d] residues | Additive Compound | Wt-% |
|---|---|---|---|---|---|---|---|---|---|---|---|---|---|---|---|---|---|
| | | | | | | | $Me_2SiCl_2$ | $MeSiCl_3$ | $Me_3SiCl$ | $HMeSiCl_2$ | $HMe_2SiCl$ | $H_2MeSiCl$ | | | | | |
| 47 | $(Bu_3P)_2NiCl_2$ | 0.2 | 750 | 100 | 7.5 | 69 | 21 | 10 | tr | 29 | tr[e] | 6 | 66 | 35 | 3 | | |

[a]The present yields are rounded to the nearest percent.
[b]Nitrogen pressure rather than hydrogen pressure.
[c]"NA" denotes "not analyzed".
[d]Wt. % residues = Percent of starting material converted − Percent of total monomers obtained.
[e]"tr" denotes "trace" (less than 1%).
[f]Disilanes with all normally accompanying solids removed.
[g]Disilanes with abnormal amount of accompanying solids.
[h]Ten-fold scale up in materials and autoclave.
[i]Deactivated, non-pyrophoric.
[j]50% Ni, Girdler Catalyst No. G-49B.
[k]50% Ni, 2% Zr, Girdler Catalyst No. G-69.
[l]Product of 2 Bu$_3$P and 1 CuCl$_2$ in methanol.
[m]"φ" denotes phenyl group.

The results as presented in Table I show copper to be an effective hydrogenation catalyst in various forms, including CuCl (Runs 14 - 19), copper powder (Runs 20 - 21), CuCl in the presence of AlCl$_3$ (Runs 22 - 24), CuCl in the presence of ZnCO$_3$ (Runs 25 - 26), the complex prepared from tributyl phosphine and copper chloride (Runs 35 - 36), and (Me$_2$NCH$_2$CH$_2$NMe$_2$)CuCl$_2$ (Run 40).

It is to be noted that high yields of hydrosilane monomers are obtained using 1 wt. % CuCl catalyst based on the weight of polysilane reactant at 350° C and 1000 psig with a reaction time of 1 hour (see Runs 14 - 16 wherein hydrosilane monomer yields are 60%, 55%, and 51% respectively). It should also be noted that a high total yield of hydrosilane monomers (55% yield) is obtained using a very small amount of copper catalyst (0.44 wt. % of copper powder based upon the weight of the polysilane reactant - see Run 20). Moreover, Run 36 provides a high yield of hydrosilane monomers (56%) under mild conditions (600 psig H$_2$, 150° C) using a small amount of copper catalyst (1 wt. % of 2Bu$_3$P·CuCl$_2 \approx$ 0.12 wt. % net copper).

It is surprising that copper provides a hydrogenation catalyst for polysilanes that is comparable in effectiveness to that of Raney nickel — long considered to be an excellent hydrogenation catalyst — under similar reaction conditions. For example, Run 20 using 0.44 wt. % copper powder catalyst provides the same yield of hydrosilanes as is provided in Run 29 using 0.4 wt. % Raney nickel catalyst (55% hydrosilanes) under identical conditions.

EXAMPLE 2

The product mixture obtained using Run 17 (wherein 430 grams of a disilane mixture was reacted in a 3-liter rocking autoclave) was distilled to give 326 grams of a mixture of monomeric silanes, 77 grams of a mixture of disilanes, and 2% of a residue. The recovered disilane mixture was divided into two parts. One half of the disilane mixture was reacted with hydrogen at 1000 psig in the presence of a copper chloride catalyst. The other half of the disilane mixture was reacted with hydrogen at 1000 psig in the presence of a Raney nickel catalyst. A determination was made of the extent of reaction for each catalyst and of the amount of unreacted disilane which was available for further reaction by recycling. The results are presented in Table II below.

TABLE II

| Catalyst | 1 wt. % CuCl | 0.4 wt. % Ni |
|---|---|---|
| Reaction Temperature | 325° C | 350° C |
| Reaction Time | 2.5 hours | 1 hour |
| Weight Percent Monomer Products | | |
| H$_2$MeSiCl | 3 | 6 |
| HMe$_2$SiCl | 3 | 2 |
| HMeSiCl$_2$ | 15 | 21 |
| Me$_3$SiCl | 2 | 2 |
| MeSiCl$_3$ | 8 | 9 |
| Me$_2$SiCl$_2$ | 6 | 9 |
| Percent Conversion | 40–50 | 70 |

EXAMPLE 3

In order to determine whether the obtaining of the products H$_2$MeSiCl, MeSiCl$_3$, and HMeSiCl$_2$ was dependent upon redistribution reactions (such as H$_2$MeSiCl + MeSiCl$_3 \rightleftarrows$ 2 HMeSiCl$_2$), an experiment was carried out using a product mixture containing 12 wt. % MeSiCl$_3$ (more than normally expected to be found in a product mixture. See Run 28 where ~ 8 wt. % MeSiCl$_3$ was formed). After 1 hour at 350° C in the presence of 0.4 wt. % Raney nickel catalyst, the yield of new monomers was given in Table III. As can be seen by comparison with the results of Run 28, no substantial change in product distribution had occurred (note especially the amounts of H$_2$MeSiCl and new MeSiCl$_3$ formed).

TABLE III

| | Wt. Percent Yield | |
|---|---|---|
| Monomer | Example 3 | Run 28 (Table I) |
| H$_2$MeSiCl | 11 | 13 |
| HMe$_2$SiCl | 6 | 8 |
| HMeSiCl$_2$ | 38 | 37 |
| Me$_3$SiCl | 3 | 3 |
| MeSiCl$_3$ | 5 | 8 |
| Me$_2$SiCl$_2$ | 24 | 18 |
| Percent conversion | 96 | 91 |

EXAMPLE 4

Fifty pounds of a mixture of polysilanes obtained as by-products of the reaction of silicon with methyl chloride and comprising 9.1 wt. percent of compounds having a boiling point of less than 149° C, 3.3 percent with a boiling point of greater than 159° C, 4.2 percent of Me$_4$Si$_2$Cl$_2$, and 83.5 percent of a mixture of Me$_3$Si$_2$Cl$_3$ and Me$_2$Si$_2$Cl$_4$, was charged into a 50 gallon stirred autoclave. The 2Bu$_3$P·CuCl$_2$ catalyst was added (225 grams, 1 wt. percent), and 600 psig hydrogen pressure was applied at 25° C. The resulting molar ratio of H$_2$: disilanes was about 0.5:1. The mixture was heated to 150° C and an 800 psig pressure was maintained by hydrogen addition during the ensuing 6.5 hour reaction period. After cooling and venting, the following product mixture resulted:

| | |
|---|---|
| H$_2$MeSiCl | 9.2 wt. % |
| HMe$_2$SiCl | 1.2 |
| HMeSiCl$_2$ | 37.4 |
| Me$_3$SiCl | 0.6 |
| MeSiCl$_3$ | 12.8 |
| Me$_2$SiCl$_2$ | 17.8 |
| compounds bp 71° - 149° | 13.4 |
| Me$_4$Si$_2$Cl$_2$ | 3.6 |
| Me$_3$Si$_2$Cl$_3$ + Me$_2$Si$_2$Cl$_4$ | 0.8 |
| compounds bp > 159° | 2.5 |

EXAMPLE 5

Another reaction was performed at 1 atmosphere hydrogen pressure in the liquid phase to obtain hydrosilanes from polysilanes. A 200 milliliter flask was equipped with a magnetic stirrer, thermometer, coarse-grade filter stick, and a 6 inch Vigreaux column topped in turn by an 8 × 0.6 inch tube that opened at the top to a surrounding water-jacketed space having a drain line at the bottom. After flushing the flask with nitrogen and adding 1 gram of (Bu$_3$P)$_2$·NiCl$_2$ to the flask, 104 grams of the polysilane mixture used in the Runs of Table I were charged into the flask and a hydrogen flow was begun through the filter stick at 145 milliliters per minute. The mixture was heated to 90° C and maintained in the range of 89° - 104° C for 4.5 hours, during which time 36.1 grams of monomers were collected. There was obtained 68.5 grams of residue comprising no more than traces of monomers and disilanes except for the mainly unreacted compounds Me$_2$ClSiSiClMe$_2$ and Me$_3$SiSiClMe$_2$. The monomer mixture contained the following silanes:

| Monomer | Yield (wt. percent) |
|---|---|
| H$_2$MeSiCl | 3.9 |
| HMe$_2$SiCl | tr |
| HMeSiCl$_2$ | 15.5* |
| Me$_3$SiCl | 4.5 |
| MeSiCl$_3$ | 31.7 |
| Me$_2$SiCl$_2$ | 44.5 |

*Reactant contained 5.4 wt. percent HMeSiCl$_2$

The reaction was repeated at 100° C and 150° C using 2 wt. percent of the copper catalyst. Except during an initial period when Me$_3$SiSiMeCl$_2$ was selectively consumed, no significant amount of hydrosilanes was produced.

EXAMPLE 6

Reactions were performed at 1 atmosphere pressure in the vapor phase over a nickel on kieselguhr catalyst and a copper on aluminum oxide (Cu/Al$_2$O$_3$) catalyst, and the results were compared with a standard run in the absence of a catalyst. The catalyst chips were placed in a vertical, resistance heated Vycor reactor tube containing an annular thermocouple well having an effective volume of 1.4 cubic centimeter per centimeter of reactor length and activated with hydrogen at 40 milliliters per minute at 500°–650°. The reaction was begun at 550° C by pumping the polysilane mixture (see Example 1 for the composition of the polysilane mixture) at rates which provided 10 to 32 seconds contact time, based on free volume, and at molar ratios of H$_2$ to disilanes of 1.0 to 7.7, as determined from the gas and liquid feed rates. The ranges of molar ratios of products obtained per mole of MeSiCl$_3$ using the nickel catalyst were HMeSiCl$_2$, 0.56–0.77; HMe$_2$SiCl, 0.19–0.44; and Me$_2$SiCl$_2$, 0.71–0.83 at 74–100% conversion of the tri and tetrachlorodisilane components. Similar results were obtained using the copper catalyst, except that more Me$_2$SiCl$_2$ than MeSiCl$_3$ was obtained. A comparison of the catalyzed reaction versus the uncatalyzed standard follows:

|  | Ni/Kieselguhr | Standard No Catalyst |
|---|---|---|
| ° C | 550 | 550 |
| Contact time, seconds | 17 | 15 |
| Molar ratio of hydrogen to disilanes | 7.7 | 5.0 |
| wt. percent yield |  |  |
| H$_2$MeSiCl | 4.4 | 1.5 |
| HMe$_2$SiCl | 7.2 | 9.3 |
| HMeSiCl$_2$ | 19.6 | 12.5 |
| Me$_3$SiCl | 2.4 | 3.8 |
| MeSiCl$_3$ | 33.5 | 27.0 |
| Me$_2$SiCl$_2$ | 21.4 | 30.0 |
| Wt. percent unreacted disilanes | 11.5 | 16.0 |
| Wt. percent yield hydrosilanes | 31.2 | 23.3 |

EXAMPLE 7

This experiment was carried out to determine whether a recovered liquid catalyst concentrate could be reused effectively in a subsequent reaction. A mixture (which had previously been heated for 7 hours at 100° C under 750 psig of hydrogen with only 22 wt. percent conversion of disilanes and formation of only 4 wt. percent monomers) of 50 grams of polysilane reactants (see Example 1 for the composition of the polysilane reactants) and 1 wt. percent of 2Bu$_3$P.CuCl$_2$ catalyst was heated at 150° C under 600 psig of hydrogen at 25° C for 6 hours whereupon Mixture A resulted. Mixture A was then distilled at 60° C and 15 millimeters of Hg along with 5 grams of the 8 grams analytical sample removed following the 100° C treatment. The residue was cooled under nitrogen when disilanes began to reflux in the head of the reactor. Nine grams of combined polysilanes and catalyst was mixed with 40 grams of fresh disilane mixture and treated under 600 psig of hydrogen for 6 hours at 150° C. Mixture B was obtained, demonstrating that the catalyst was substantially effective upon reuse.

|  | Mixture A | Mixture B |
|---|---|---|
| Wt. Percent H$_2$MeSiCl | 12 | 12 |
| HMe$_2$SiCl | tr | tr |
| HMeSiCl$_2$ | 42 | 34 |
| Me$_3$SiCl | 2 | 1 |
| MeSiCl$_3$ | 12 | 17 |
| MeSiCl$_2$ | 16 | 17 |
| Total monomers | 84 | 81 |
| Total hydrosilanes | 54 | 46 |
| Percent conversion | 86 | 93 |
| Percent residue | 2 | 12 |

What is claimed is:

1. A process for preparing silanes of the formula H$_a$Me$_x$SiCl$_{4-(a+x)}$, comprising
A. contacting
(1) a polysilane consisting of units of the formula:

Me$_x$Cl$_y$Si            (I), with
(2) hydrogen gas under pressure, and
B. heating the above admixture to a temperature of from about 25° C to about 350° C, in the presence of a catalytic amount of a copper catalyst,
wherein $a$ is 1 to 2, $x$ is 0 to 3, and $y$ is 0 to 3, the sum of $a$ and $x$ being from 1 to 4, the sum of $x$ and $y$ being from 1 to 3; all the silicon atoms in (I) being bonded to at least one other silicon atom and all the valences of the silicon atoms in (I) being satisfied by other silicon atoms, Cl or Me radicals, with the proviso that the polysilane contain at least one Cl group.

2. The process of claim 1 wherein the catalyst is copper metal.

3. The process of claim 1 wherein the catalyst is cuprous chloride.

4. The process of claim 1 wherein the catalyst is a trialkylphosphine complex of a copper salt.

5. The process of claim 1 wherein the catalyst is the product of the reaction of two moles of tributylphosphine with one mole of cupric chloride.

6. The process of claim 1 wherein the polysilane is Cl$_2$CH$_3$SiSiCH$_3$Cl$_2$.

7. The process of claim 1 wherein the polysilane is Cl$_2$CH$_3$SiSi(CH$_3$)$_2$Cl.

8. The process of claim 1 wherein the polysilane is Cl(CH$_3$)$_2$SiSi(CH$_3$)$_2$Cl.

* * * * *

UNITED STATES PATENT OFFICE
CERTIFICATE OF CORRECTION

Patent No. 4,079,071    Dated 3/14/78

Inventor(s) R. S. Neale

It is certified that error appears in the above-identified patent and that said Letters Patent are hereby corrected as shown below:

In Table I, in the left-most column, "No." should read ---Run No.--- (Patent columns 5 and 7, bottom).

In Table I, in the column second-to-the-left, for Run No. 41, the formula "$(C_{16}H_{33}NMe_2)_2CuCl_3$" should read ---$(C_{16}H_{33}NMe_2)_2CuCl_2$--- (Patent column 6, near the bottom).

In column 9, line 22, the word "net" should read ---*net*---.

Signed and Sealed this

*Twenty-seventh* Day of *June 1978*

[SEAL]

*Attest:*

RUTH C. MASON
*Attesting Officer*

DONALD W. BANNER
*Commissioner of Patents and Trademarks*